United States Patent
Farooq et al.

(10) Patent No.: US 10,403,391 B2
(45) Date of Patent: Sep. 3, 2019

(54) AUTOMATED MAPPING OF SERVICE CODES IN HEALTHCARE SYSTEMS

(71) Applicant: Cerner Health Services, Inc., Wilmington, DE (US)

(72) Inventors: Faisal Farooq, Norristown, PA (US); Joseph M. Overhage, Zionville, IL (US); Glenn Fung, Madison, WI (US); Shipeng Yu, Exton, PA (US); R. Bharat Rao, Berwyn, PA (US); Balaji Krishnapuram, King of Prussia, PA (US); Jan DeHaan, Hawley, PA (US)

(73) Assignee: Cerner Health Services, Inc., Wilmington, DE (US)

( * ) Notice: Subject to any disclaimer, the term of this patent is extended or adjusted under 35 U.S.C. 154(b) by 100 days.

(21) Appl. No.: 14/037,548

(22) Filed: Sep. 26, 2013

(65) Prior Publication Data
US 2014/0095205 A1    Apr. 3, 2014

Related U.S. Application Data

(60) Provisional application No. 61/707,288, filed on Sep. 28, 2012.

(51) Int. Cl.
*G16H 80/00* (2018.01)
*G16H 10/60* (2018.01)

(52) U.S. Cl.
CPC .................. *G16H 10/60* (2018.01)

(58) Field of Classification Search
CPC .............................. G16H 10/60; G16H 80/00
(Continued)

(56) References Cited

U.S. PATENT DOCUMENTS

| 5,119,465 A | 6/1992 | Jack et al. |
| 5,627,972 A | 5/1997 | Shear |

(Continued)

FOREIGN PATENT DOCUMENTS

| EP | 0 722 140 A1 | 7/1996 |
| GB | 2 320 111 A | 6/1998 |

(Continued)

OTHER PUBLICATIONS

Mustafa Fidahussein, Daniel J Vreenman, "A corpus-based approach for automated LOINC mapping", J Am Med Inform Assoc 2013; 0:1-9 doi:10.1136/amiajnl-2012-001159.

(Continued)

*Primary Examiner* — John A Pauls
(74) *Attorney, Agent, or Firm* — Shook, Hardy & Bacon L.L.P.

(57) ABSTRACT

Automatic mapping of semantics in healthcare is provided. Data sets have different semantics (e.g., Gender designated with M and F in one system and Sex designated with 1 or 2 in another system). For semantic interoperability, the semantic links between the semantic systems of different healthcare entities are created (e.g., Gender=Sex and/or 1=F and 2=M) by a processor from statistics of the data itself. The distribution of variables, values, or variables and values, with or without other information and/or logic, is used to create a map from one semantic system to another. Similar distributions of other variable and/or values are likely to be for variables and/or values with the same meaning.

23 Claims, 2 Drawing Sheets

(58) Field of Classification Search
USPC .............................. 705/3; 707/780; 715/224
See application file for complete search history.

(56) References Cited

U.S. PATENT DOCUMENTS

| | | | |
|---|---|---|---|
| 5,694,578 A | 12/1997 | Upson et al. |
| 5,712,989 A | 1/1998 | Johnson et al. |
| 5,715,453 A | 2/1998 | Stewart |
| 5,724,575 A | 3/1998 | Hoover et al. |
| 5,738,102 A | 4/1998 | Lemelson |
| 5,740,425 A | 4/1998 | Povilus |
| 5,911,776 A | 6/1999 | Guck |
| 5,913,210 A | 6/1999 | Call |
| 5,935,060 A | 8/1999 | Iliff |
| 5,987,472 A | 11/1999 | Serafin |
| 6,055,516 A | 4/2000 | Johnson et al. |
| 6,058,375 A | 5/2000 | Park |
| 6,081,786 A | 6/2000 | Barry et al. |
| 6,085,203 A | 7/2000 | Ahlers et al. |
| 6,112,209 A | 8/2000 | Gusack |
| 6,134,515 A | 10/2000 | Skogby |
| 6,138,183 A | 10/2000 | Tien et al. |
| 6,151,702 A | 11/2000 | Overturf et al. |
| 6,152,612 A | 11/2000 | Liao et al. |
| 6,154,738 A | 11/2000 | Call |
| 6,195,664 B1 | 2/2001 | Tolfa |
| 6,212,526 B1 | 4/2001 | Chaudhuri et al. |
| 6,301,584 B1 | 10/2001 | Ranger |
| 6,418,441 B1 | 7/2002 | Call |
| 6,430,541 B1 | 8/2002 | Brown et al. |
| 6,430,554 B1 | 8/2002 | Rothchild |
| 6,454,738 B1 | 9/2002 | Call |
| 6,468,210 B1 | 10/2002 | Iliff |
| 6,510,434 B1 | 1/2003 | Anderson et al. |
| 6,510,989 B1 | 1/2003 | Ortega |
| 6,523,019 B1 | 2/2003 | Borthwick |
| 6,535,874 B2 | 3/2003 | Purcell |
| 6,542,933 B1 | 4/2003 | Durst et al. |
| 6,551,243 B2 | 4/2003 | Bocionek et al. |
| 6,551,266 B1 | 4/2003 | Davis, Jr. |
| 6,578,030 B1 | 6/2003 | Wilmsen et al. |
| 6,587,829 B1 | 7/2003 | Camarda et al. |
| 6,641,532 B2 | 11/2003 | Iliff |
| 6,708,161 B2 | 3/2004 | Tenorio et al. |
| 6,714,913 B2 | 3/2004 | Brandt et al. |
| 6,728,950 B2 | 4/2004 | Davis et al. |
| 6,775,660 B2 | 8/2004 | Lin et al. |
| 6,785,671 B1 | 8/2004 | Bailey et al. |
| 6,792,431 B2 | 9/2004 | Tamboli et al. |
| 6,801,227 B2 | 10/2004 | Bocioned |
| 6,903,194 B1 | 6/2005 | Sato et al. |
| 7,062,509 B1 | 6/2006 | Nenov et al. |
| 7,130,457 B2 | 10/2006 | Kaufman et al. |
| 7,310,607 B2 | 12/2007 | Brandt et al. |
| 7,343,551 B1 * | 3/2008 | Bourdev ............... G06F 17/243 715/224 |
| 7,438,216 B2 | 10/2008 | Ambekar et al. |
| 7,447,644 B2 | 11/2008 | Brandt et al. |
| 7,451,096 B2 | 11/2008 | Rucker |
| 7,617,078 B2 | 11/2009 | Rao et al. |
| 7,653,873 B2 | 1/2010 | Brandt et al. |
| 7,689,441 B1 | 3/2010 | Craft |
| 7,765,114 B2 | 7/2010 | Frick |
| 7,810,045 B2 | 10/2010 | Weber |
| 7,895,055 B2 | 2/2011 | Schneider et al. |
| 7,908,153 B2 | 3/2011 | Schierpbier et al. |
| 8,364,499 B2 | 1/2013 | Maughan et al. |
| 8,392,232 B2 | 3/2013 | McGillin |
| 8,554,480 B2 | 10/2013 | Grigsby et al. |
| 2001/0029492 A1 | 10/2001 | Uchikata |
| 2002/0059107 A1 | 5/2002 | Reich et al. |
| 2002/0059204 A1 | 5/2002 | Harris |
| 2002/0099622 A1 | 7/2002 | Langhammer |
| 2002/0107861 A1 | 8/2002 | Clendinning et al. |
| 2002/0111870 A1 | 8/2002 | Chinnappan et al. |
| 2002/0161745 A1 | 10/2002 | Call |
| 2002/0161749 A1 | 10/2002 | Pratt |
| 2003/0036683 A1 | 2/2003 | Kehr et al. |
| 2003/0046114 A1 | 3/2003 | Davies et al. |
| 2003/0115129 A1 | 6/2003 | Feaver et al. |
| 2003/0120133 A1 | 6/2003 | Rao et al. |
| 2003/0120134 A1 | 6/2003 | Rao et al. |
| 2003/0120458 A1 | 6/2003 | Rao et al. |
| 2003/0120514 A1 | 6/2003 | Rao et al. |
| 2003/0125984 A1 | 7/2003 | Rao et al. |
| 2003/0125985 A1 | 7/2003 | Rao et al. |
| 2003/0125988 A1 | 7/2003 | Rao et al. |
| 2003/0126101 A1 | 7/2003 | Rao et al. |
| 2003/0130871 A1 | 7/2003 | Rao et al. |
| 2003/0177111 A1 | 9/2003 | Egendorf et al. |
| 2003/0212580 A1 | 11/2003 | Shen |
| 2004/0059728 A1 | 3/2004 | Miller et al. |
| 2004/0172297 A1 | 9/2004 | Rao et al. |
| 2004/0205611 A1 | 10/2004 | Minninger |
| 2005/0261941 A1 | 11/2005 | Scarlat |
| 2006/0122865 A1 | 6/2006 | Preiss et al. |
| 2008/0275731 A1 | 11/2008 | Rao et al. |
| 2009/0018882 A1 | 1/2009 | Burton et al. |
| 2009/0076839 A1 | 3/2009 | Abraham-Fuchs et al. |
| 2011/0047176 A1 | 2/2011 | Hoffman |
| 2011/0077972 A1 | 3/2011 | Breitenstein et al. |
| 2011/0077973 A1 | 3/2011 | Breitenstein et al. |
| 2011/0295622 A1 | 12/2011 | Farooq et al. |
| 2012/0065987 A1 | 3/2012 | Farooq et al. |
| 2012/0065997 A1 | 3/2012 | Farooq et al. |
| 2012/0110016 A1 * | 5/2012 | Phillips .................... 707/780 |
| 2012/0166226 A1 | 6/2012 | Lee et al. |
| 2012/0174018 A1 | 7/2012 | Ash |
| 2012/0231959 A1 | 9/2012 | Elton et al. |
| 2013/0085780 A1 | 4/2013 | Braunstein et al. |
| 2013/0173290 A1 | 7/2013 | Owings |
| 2013/0290020 A1 | 10/2013 | Brush |
| 2014/0100880 A1 | 4/2014 | Patterson et al. |

FOREIGN PATENT DOCUMENTS

| | | |
|---|---|---|
| WO | 9832289 A2 | 7/1998 |
| WO | 01/06357 A1 | 1/2001 |

OTHER PUBLICATIONS

Kenneth A Zollo, et al., "Automated Mapping of Observation Codes Using Extensional Definitions", Journal of the American Medical Informatics Association, vol. 7, No. 6, Nov./Dec. 2000.

Ming-Chin Lin, et al., "Investigating the Semantic Interoperability of Laboratory Data Exchanged Using LOINC Codes in Three Large Institutions", AMIA Annu Symp Proc. 2011; 2011: 805-814. Published online Oct. 22, 2011.

M.C. Lin, et al., "Auditing consistency and usefulness of LOINC use among three large institutions—Using version spaced for groupoing LOINC codes", Journal of Biomedical Informatics, vol. 45, Issue 4, Aug. 2012, pp. 658-666.

Kamp, et al. "Database system support for multidimensional data analysis in environmental epidemiology", The 1997 International Database Engineering & Applications Symposium; Montreal; Can; Aug. 25-27, 1997. pp. 180-188. 1997.

King, et al., "MEDUS/A: Distributing Database Management for Medical Research", Proceedinngs of Computer Networks Compcon 82, 20.09.1982-23.09.1982 pp. 635-642.

Boxwala et al, "Architecture for a Multipurpose Guideline Execution Engine", Proc. AMIA Symp 1999, pp. 701-705.

"Guidance for Institutional Review Boards and Clinical Investigators 1998 Update", Sep. 1998, U.S. Food and Drug Administration, http://www.fda.gov/ScienceResearch/SpecialTopics/RunningClinicalTrials/GuidancesInformationSheetsandNotices/ucm113793.htm#IRBMember.

Kassirer, "The Use and Abuse of Practice Profiles", The New England Journal of Medicine, vol. 330:634-636, Mar. 3, 1994.

Chen, et al., Do "America's Best Hospitals" Perform Better for Acute Myocardial Infarction?, The New England Journal of Medicine, vol. 340, No. 4:286-292, Jan. 28, 1999.

(56) References Cited

OTHER PUBLICATIONS

Hofer, et al., "The Unreliability of Individual Physician 'Report Cards' for Assessing the Costs and Quality of Care of a Chronic Disease", JAMA, Jun. 9, 1999, vol. 281, No. 22, pp. 2098-2105.
Ong et al, "The Colorectal Cancer Recurrence Support (CARES) System; Artificial Intelligence in Medicine", Nov. 1997, Elsevier, Netherlands, vol. 11, pp. 175-188.
Nahm, et al., "A Mutually Beneficial Integration of Data Mining and Information Extraction", In Proceedings of the Seventeenth National Conference on Artificial Intelligence (AAAI-2000), Jul. 30, 2000, pp. 627-632, Austin, TX, 20001.
Rao, et al., "Data mining for disease management: adding value to patient records", Electromedica, vol. 68, 2000, pp. 63-67.
Mills, "Computer Technology of the Not-Too-Distant Future" Sep. 1993, Medical Laboratory Observer, vol. 25, No. 9, p. 78.
Duda, et al., "Pattern Classification—Chapter 1" 2001, John Wiley & Sons, New York, US, XP002536377, pp. 14-17.
Hudson, et al., "The Feasibility of Using Automated Data To Assess Guideline-Concordant Care for Schizophrenia", Journal of Medical Systems, vol. 23 No. 4 1999, pp. 299-307.
PR Newswire, "Diabetes Health Management Award Honors Mayo Clinic's Zimmerman", Sep. 25, 2000, http://www.thefreelibrary.com/Diabetes Health Management Award Honors Mayo Clinic's Zimmerman.-a065465402.
Hudson, Mary E., "CAATS and compliance—computer-assisted audit techniques in health care", Internal Auditor, Apr. 1998, vol. 55, No. 2, p. 25, http://findarticles.com/p/articles/mi_m4153/is_n2_v55/ai_20860208/.
Grimes, Seth, "Structure, Models and Meaning, Is 'Unstructured' data merely unmodeled?", Intelligent Enterprise, Mar. 2005, http://intelligent-enterprise.informationweek.com/showArticle.jhtml?articleID=59301538.
Berkus, "Unstructured Data as an Oxymoron", ITtoolbox Blogs, Sep. 1, 2005, http://it.toolbox.com/blogs/database-soup/unstructured-data-as-an-oxymown-5588.
Larsen, "Fast and Effective Test Mining Using Linear-time Document Clustering", In Knowledge Discovery and Data Mining (1999), pp. 16-22.
Rao, "From Unstructured Data to Actionable Intelligence", IT Pro, Nov./Dec. 2003, pp. 29-35.
Mitchell, "Machine Learning and Data Mining", Communications of the ACM, Nov. 1999, vol. 42, No. 11, pp. 31-36.
Kleissner, "Data Mining for the Enterprise", System Sciences, 1998, Proceedings of the Thirty-First Hawaii International Conference on Kohala Coast, HI, Jan. 6-9, 1998, IEEE Comput. Soc. US, pp. 295-304.
Evans, et al., "Using Data Mining to Characterize DNA Mutations by Patient Clinical Features", Proc AMIA Annu Fall Symp. 1997: 253-257.
Waltz, "Information Understanding Integrating Data Fusion and Data Mining Processes", Circuits and Systems, 1998, Proceedings of the 1998 IEEE International Symposium in Monterey, CA, USA, May 31-Jun. 3, 1998, NY, NY, May 31, 1998, pp. 553-556.
Roemer, et al., "Improved diagnostic and prognostic assessments using health management information fusion," AUTOTESTCON Proceedings, 2001. IEEE Systems Readiness Technology Conference , vol., No., pp. 365-377, 2001.
Chemical and Biological Arms Control Institute: "Bioterrorism in the United States:Threat, Preparedness and Response", Contract No. 200*1999*00132, Nov. 2000.

Hanson, et al.. "Probabilistic Heuristic Estimates", Annals of Mathematics and Artificial Intelligence, vol. 2, Nos. 1-4, pp. 209-220, 1990.
Stephen F. Jencks, MD., M.P.H., et al., "Rehospitalizations among Patents in the Medicare Fee-for-Service Program," The New England Journal of Medicine, pp. 1418-1428, Apr. 2009.
Report to Congress, "Promoting Greater Efficiency in Medicare," MedPac, pp. 288, Jun. 2007.
Eleanor Herriman, et al., "Patient Non-adherence—Pervasiveness, Drivers, and Interventions," Sciences Spotlight Series, vol. 2, No. 4, Aug. 2007.
Cook, et al., "The Importance of medication adherence: from the doctor patient interaction to impact on health outcomes," The Forum 10, Oct. 13-15, 2010.
Gordon K. Norman, "It Takes More than Wireless to Unbind Healthcare," Presentation at Healthcare Unbound 2007 Conference (Abstract).
Lee Jacobs, "Are Your Patients Taking What You Prescribe? A Major Determinant: Clinician-Patient Communication," Physician Work Environment, vol. 6, No. 3, Summer 2002.
Michael P. Ho et al., "Impact of Medication Therapy Discontinuation on Mortality After Myocardial Infarction," Archives of Internal Medicine, 166: 1842-1847, 2007 (Abstract only).
Sergio B. Wey, et al., "Risk Factors for Hospital-Acquired Candidemia," A Matched Case Control Study, Archives of Internal Medicine, 1989;149(10), (abstract only).
Andrew Pollack, "Rising Threat of Infections Unfazed by Antibiotics," New York Times, Feb. 27, 2010.
http://en.wikipedia.org/wiki/Nosocomial infection, downloaded Jun. 2, 2011.
Janice Morse, "Preventing Patient Falls," Sage Publications, 1997.
Ann Hendrich, "How to Try This: Predicting Patient Falls," American Journal of Nursing, Nov. 2007, vol. 107, No. 11, pp. 50-58.
Philbin et al., "Prediction of Hospital Readmission for Heart Failure: Development of a Simple Risk Score Based on Administrative Data", Journal of the American College of Cardiology vol. 33, No. 6, 1999.
L. Akoglu, et al., "OddBall: Spotting Anomalies in Weighted Graphs," Carnegie Mellon University, School of Computer Science, pp. 1-12, 2010.
J. Hu Ph.D., et al., "A Healthcare Utilization Analysis Framework for Hot Spotting and Contextual Anomaly Detection," Annual Symposium Proceedings/AMIA Symposium, pp. 1-10, 2012.
Yasuko Matsubara, Lei Li, Evangelos Papalexakis, David Lo, Yasushi Sakurai, Christos Faloutsos , "F-Trail: Finding Patterns in Taxi Trajectories" Advances in Knowledge Discovery and Data Mining Lecture Notes in Computer Science vol. 7818, 2013, pp. 86-98.
"SQLData SOAP Server" © Jan. 25, 2001 SQLData Systems Inc. http://web.archive.org/web/20010202090100/http://sqldata.com/soap.htm.
"SOAP for Java" © Apr. 28, 2000 IBM. http://www.alphaworks.ibm.com/tech/soap4j/.
"Simple Object Access Protocol (SOAP) 1.1" © May 8, 2000 W3C et al. http://www.w3.org/TR/2000/Note-SOAP-200005081.
e*Index™ Global Identifier-Know Your Customer See Beyond-Products.
e*Index™ Global Identifier-In Depth See Beyond-Products.
eBusiness Integration—Its not just B2B See Beyond-Products.
Non-Final Office Action received for U.S. Appl. No. 09/973,349, dated Feb. 3, 2004, 17 pages.
Office Action dated Jun. 29, 2018 in U.S. Appl. No. 14/574,475, 18 pages.

\* cited by examiner

AUTOMATED MAPPING OF SERVICE CODES IN HEALTHCARE SYSTEMS

RELATED APPLICATION

The present patent document claims the benefit of the filing dates under 35 U.S.C. § 119(e) of Provisional U.S. Patent Application Ser. No. 61/707,288, filed Sep. 28, 2012, which is hereby incorporated by reference.

FIELD

The present embodiments relate to automated or semi-automated mapping of service codes in healthcare systems. Mappings of the codes are created automatically or semi-automatically.

BACKGROUND

There has been a considerable rise in need for interoperability of data in the healthcare system. This is either to reduce costs or increase care quality. In hospital or health information exchange (HIE) and global healthcare networks or for healthcare research where statistics and cohorts are to be derived from large populations matching certain criteria, data from different collections may be combined or exchanged. To be useful, the data must be interoperable. The criteria are defined in a semantically similar manner or somehow translated from different sources into a standard semantic representation such that searches can be performed seamlessly.

Semantic interoperability allows computer systems to transmit data with unambiguous, shared meaning. Semantic interoperability enables machine computable logic, inferencing, knowledge discovery, and/or data federation between information systems. Semantic interoperability provides for the packaging of data (syntax) and the simultaneous transmission of the meaning with the data (semantics). The information and the meaning of the information may be shared.

As part of the healthcare reform, the meaningful use guidelines regulate interoperability of data. The first phase requirement is just for lab data, but will extend to other data (clinical, demographic, and/or financial) in the future. However, many information systems or data sets at different healthcare entities are not semantically interoperable. To exchange information, a manual mapping or translation is used. For large amounts of data available in the medical field, manual mapping or translation is costly, time consuming, and error prone.

SUMMARY

By way of introduction, the preferred embodiments described below include methods, instructions, and systems for automatic mapping of semantics in healthcare. Data sets have different semantics (e.g., Gender designated with M and F in one system and Sex designated with 1 or 2 in another system). For semantic interoperability, the semantic links between the semantic systems of different healthcare entities are created (e.g., Gender=Sex and/or 1=F and 2=M) by a processor from statistics of the data itself. The distribution of variables, values, or variables and values in the data itself, with or without other information and/or logic, is used to create a map from one semantic system to another. Similar distributions of other variable and/or values are likely to be for variables and/or values with the same meaning.

In a first aspect, a method is provided for automatic mapping of semantics in healthcare. First transaction data of a first healthcare entity in a first database is accessed. The first transaction data corresponds to a first semantic system. A processor calculates a first distribution of information in the first transaction data. Second transaction data of a second healthcare entity in a second database is accessed. The second transaction data corresponds to a second semantic system different than the first semantic system. The processor calculates a second distribution of information in the second transaction data. The processor compares the first and second distributions with machine learning. The machine learning outputs a map relating the first semantic system to the second semantic system. The map being a function of the comparing.

In a second aspect, a non-transitory computer readable storage medium has stored therein data representing instructions executable by a programmed processor for automatic mapping of service codes in healthcare. The storage medium includes instructions for obtaining the service codes, the service codes having different semantics, and creating, by the programmed processor, a map relating the different semantics, the map created as a function of statistical information of the service codes.

In a third aspect, a system is provided for automatic mapping of service codes in healthcare. A memory is configured to store first medical data in a first representation and second medical data in a second representation different than the first representation. A processor is configured to link values, variables, or values and variables of the first medical data with values, variables, or values and variables of the second medical data. The links are for corresponding semantic meaning in the first and second representations.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Figure 1:
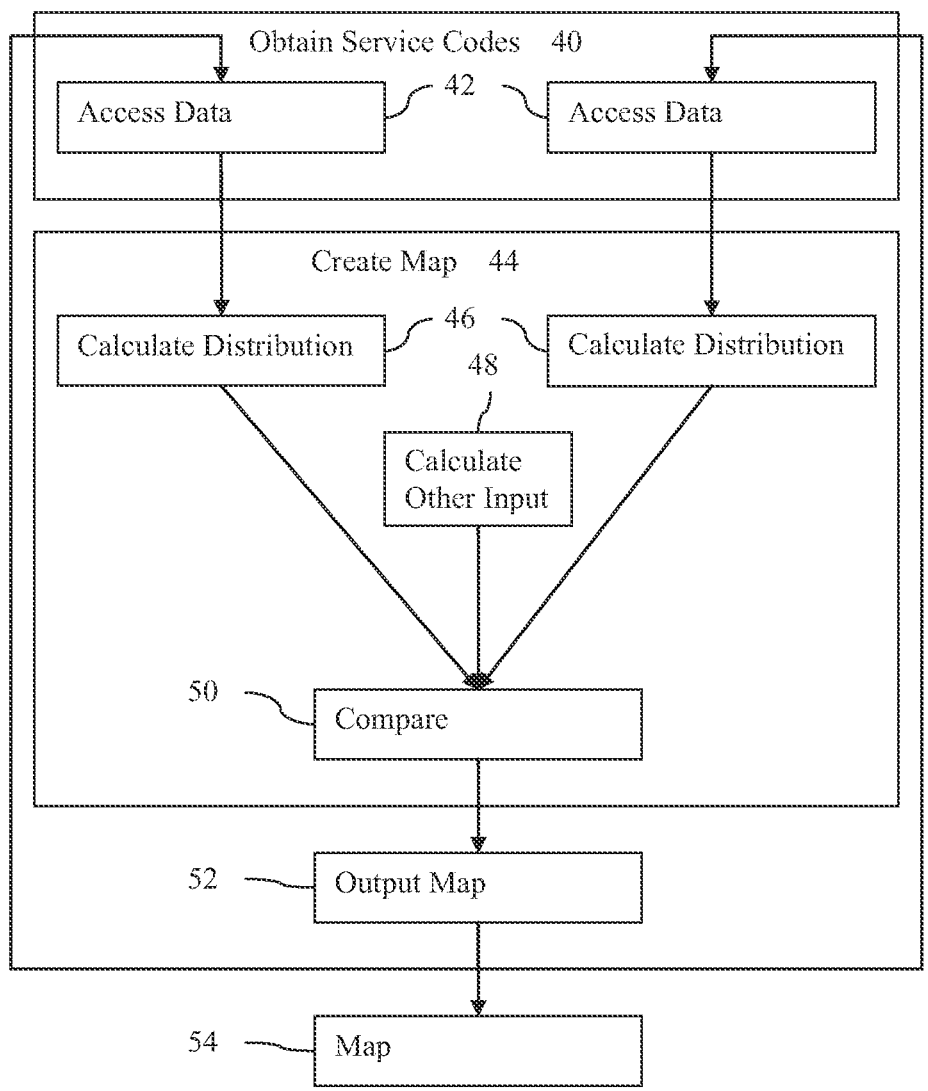
FIG. 1 is a flow chart diagram of one embodiment of a method for automatic mapping of service codes in healthcare.

Most hospital information systems including but not limited to clinical system, lab systems, departmental systems (e.g., radiology and surgery), and financial systems (coding), use their own custom representations for various services or items. For example, one system may be represented the gender field by Sex where as other system may represent it as Gender. Similarly, one system may represent the values of this field as Male, Female or Unknown, where as the other system may represent the values of this field as M, F, null, and yet another system may represent the values as 1, 2 and 0. Similarly, an order for "white blood cell count measured using flow cytometric analysis" may be represented as "CBC" in the OBR field and as "WBC" in the corresponding OBX 3 value. Some other systems may represent this order in coded numeric values which need to be understood by the source system.

In order for systems to be semantically interoperable, the transactions (order, results, service, or other medical data) from one system represented in certain format (e.g. Gender=M) has to be understood by the other system (e.g. Sex=1). The system receiving data from another system maps the data to the known semantics.

This is analogous to situations where two people have to communicate and they speak different languages or different dialects of the language. The ways to completely remove this discrepancy are:
1. System 1 sends data in the format that System 2 understands. That is System 1, which uses "Gender" as field and "M" as value, transforms this into "Sex" and "1" via an intermediate interface so that System 2 can understand. The variables and values are mapped between the two systems. This is like using a translator between the two people in the language analogy.
2. System 1 and System 2 use the same representation. It can be decided up front that field will be Gender and value will be M. This is like speaking a common language. They can be global and industry wide standards (e.g., SNOMED CT for clinical terminology or LOINC for lab codes etc). Unfortunately, most systems do not use these standards.
3. There exists a conversion (called a "map") from System 1 representation into a "standard" representation. A similar map exists between standard representation and System 2 representation. This is analogous to translating both sides into English. Note that the Method #1 is a special case of this one where the map directly exists between System 1 and System 2.

Currently most systems employ Method #1 where, in order for different systems to communicate, a map is created manually for all codes that can be communicated. This is a very manually intensive effort leading to long and expensive implementation cycles. Some systems have started employing Method #2; however, the maps to standards are still created manually.

An automatic or semi-automatic approach to creating the maps is provided. In one embodiment, Methods #1, #2, and/or #3 are automated or semi-automated. This process of creating maps between the two system terminologies is sped up by processor-based implementation, especially in the medical field where a large number of variables and value representations exist.

Figure 2:
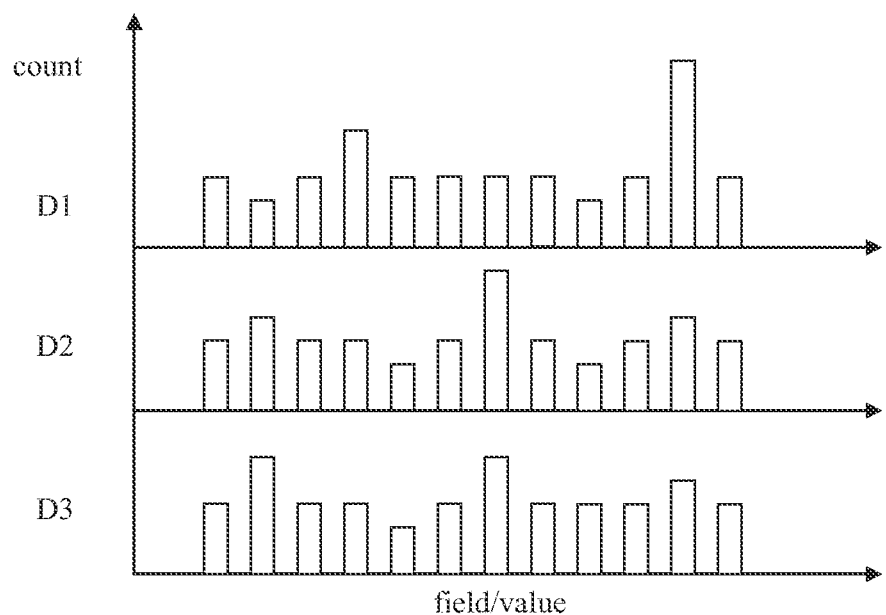
FIG. 2 shows example distributions of fields and/or values relative to a given field or value.

FIG. 2 shows a method for automatic mapping of semantics in healthcare. A processor semi-automatically or automatically creates a semantic map or relationship between different sets of medical data. Patient data, orders, services, communications, or other medical data from different healthcare systems are mapped to each other or to a standard. Statistics or distribution of the variables and/or values within the different data sets is used to link the variables and/or values having a same meaning between the data sets.

The acts of the left and right columns represent acts by different medical centers or acts performed on data from different local medical centers. Two are shown in this example, but three or more may be used. The acts in the center column represent acts by a map creation device (e.g., central server or processor of one or more medical centers). More than one map creation device may be used. The different medical centers may perform acts shown in the center column, and the device performing the acts of the center column may perform the acts of the different medical centers.

Figure 3:
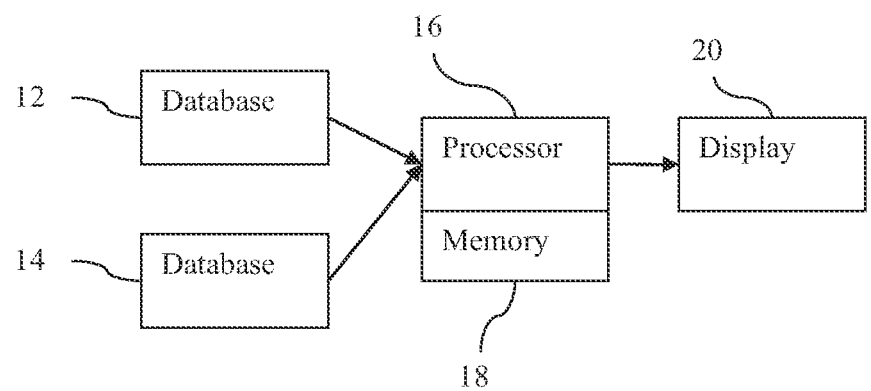
FIG. 3 is a block diagram of one embodiment of a system for automatic mapping of service codes in healthcare.

The method of FIG. 1 is implemented by the system of FIG. 3 or a different system. A processor performs the accessing, calculating, comparing, and outputting acts with or without user input for performing the acts once triggered to perform. Additional, different, or fewer acts may be provided. For example, act 48 is not provided, such as where statistics or distribution alone is used for creating the semantic map. As another example, act 54 is not performed.

In act 40, service codes are obtained. Service codes are any transaction or collection of data related to medical service. For example, a laboratory system may receive orders or other messages at an interface from an information technology system. The orders include one or more variables (e.g., CBC), may contain values (e.g., Male), and may contain descriptions (e.g., text field describing the ordered test). As another example, the laboratory system may output a response or service message indicating the test (e.g., variable of CBC) and the value (e.g., value of OBX 3) with or without other information (e.g., a text description, notes, and/or patient information). As another example, a computerized medical record may contain various types of information (e.g., variables and values for a collection of patients). The service codes may use standardized coding or use non-standard or healthcare entity specific standards. The service codes are represented by transaction data.

The service codes are obtained from different medical entities. Within a hospital or other healthcare provider, different systems or departments may use different semantics. These different systems are different medical entities. Different hospitals, healthcare facilities or networks may use different semantics, so represent different medical entities.

In act 42, the transaction data of different healthcare entities are accessed. Data related to patients is accessed. The transaction data is clinical data, such as data gathered as routine in diagnosis and/or treatment of a patient. For example, the transaction data includes billing records, physician notes, medical images, pharmacy database, lab records, and/or other information gathered about a patient. The transaction data may include requests, queries, results, acknowledgements, or other interface records. In one embodiment, messages in a HIE system represent the transaction data.

The transaction data is for a plurality of patients. The medical center collects transaction data in a database, such as a computerized patient record or system storage. The collection is in one location or distributed over multiple locations. For each patient that visits, patient data is collected. For a given condition, there may be patient data for multiple (e.g., tens, hundreds, or thousands) patients. For a given healthcare entity, there may be patient data for multiple patients.

The access at a given healthcare entity is by requests to or pushes from a database. Alternatively, communications are routed, copied or intercepted for access to the transactions, such as obtaining a copy of orders inbound to an interface or responses outbound from an interface. A separate collection of transactions may be created, or a collection existing for other purposes is used. For each healthcare entity, one or more different databases are accessed. Different databases are accessed for different entities. In alternative embodiments, the transaction data from the different healthcare entities is collected and stored in a common database.

Since the transaction data is from different healthcare entities, the transaction data being accessed is different. Due to the medical entities being in different geographic regions, having different types of patients, and/or different approaches to diagnosis and/or treatment, the transaction data is different even with the same semantics.

Where different semantics are used, the transaction data is different. Different semantic systems are used. The semantic systems correspond to different labels or use of language for the same meaning. The fields (e.g., variables) and/or values used for a same thing or concept may be different for the different semantic systems. Some of the fields and/or variables may be the same (e.g., using Gender in both but "heart attack" and "cardiac event" in the different semantic systems). The transaction data from the different healthcare entities corresponds to at least one semantic difference, so are different semantic systems.

Each medical entity may use unique and multiple information systems and differ in clinical practice including the way (e.g. language) in which data is collected. For semantic normalization, transactions are translated to a semantic interoperable environment. The normalization is performed automatically to limit usage of resources. Local medical entity terms are semantically mapped to a standard or to terms of another medical entity. For example, the terms are mapped to an ontology. For example, an ontology includes the National Cancer Institute Thesaurus, which is accessed through the open source Jena framework. Additional concepts for radiotherapy authored in the open source Protégé editor (Stanford Center for Biomedical Informatics Research, Palo Alto, Calif., USA) may be included.

The transaction data is accessed using existing routines or formats of the respective healthcare entities. Alternatively, specialized programs or formatting may be used to access. In one embodiment, the access is through data mining to reformat the transaction data. A data miner may be run using the Internet or local network. A user may control the mining without access to transaction data. The data miner creates a database of structured information relevant to the creation of the semantic mapping. The created structured clinical information may or may not also be accessed using the Internet.

The mining is performed using a domain knowledge base. The domain knowledge base may be encoded as an input to the system by manual programming or as machine-learnt programs that produce information that can be understood by the system. The data miner system uses the domain knowledge to determine what data to extract, how to extract the data, and how to determine the values, variables, linguistics, and/or other information from the data.

The domain-specific criteria for mining the data sources may include institution-specific domain knowledge. For example, this may include information about the data available at a particular medical entity, document structures at the medical entity, policies of a medical entity, guidelines of a medical entity, and/or any variations of a medical entity. The data miner is configured or programmed to access data at a given medical entity. Data miners at different medical entities may be configured as appropriate for the respective medical entity.

The domain-specific criteria may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies.

In one embodiment, a data miner includes components for extracting information from the databases of patient data (computerized patient records), combining available evidence in a principled fashion over time, and drawing inferences from this combination process. The mined medical information may be stored in the structured CPR database. Any form of data mining may be used.

In one embodiment, the system will assimilate information from both imaging and non-imaging sources within the computerized patient record (CPR). These data can be automatically extracted, combined, and analyzed in a meaningful way, and the results presented. Such a system may also help avoid mistakes, as well as provide a novice with knowledge "captured" from expert users based on a domain knowledge base of a disease of interest and established clinical guidelines.

The extraction is the same or different for each medical entity. Since the medical entities may have different policies and/or computerized patient record or other transaction systems, different extraction and/or access may be used.

In act 44, a map relating the different semantic systems to each other is created. A processor determines the variables and/or values in one semantic system that have the same meaning as variables and/or values in the other semantic system. The syntax of the data and the meaning of the data elements are related or linked to each other.

The map is created using statistical information. Statistics of the service codes indicate the semantic links. The transaction data itself is used. The mappings are derived from the statistical power of data in an automated manner. For example, if a 'demographic' field with two values is identified consistently, the probability of the field being a gender field is very high. This guess may be made initially, and refined (strengthened or weakened) as more data is obtained. As another example, assume the initial or final guess about the gender field. The field usually has 2 values, 1 and 2. Now the task is to understand whether 1 stands for male or female. Looking at other aspects of the data, an order for a pregnancy test or a breast cancer screening in the transaction data descriptions when the value of the gender field is always 2, indicates a high probability that 2 means female given that ordering such tests would be next to impossible in a male. Where the pregnancy test description is provided, this variable itself may be used to associate the 2 with female. Where the description is not provided or not trusted, the fact that the distribution other variables, including a high count for a variable related to pregnancy testing, matches in both semantic systems indicates that 2 and female are the same. This strengthens the initial link of the field to gender and/or determines the links for the values.

In one embodiment, the statistics are derived from distributions of information in the transaction data. Distributions are calculated for each set of transaction data (e.g., for each semantic system) in act 46. The distribution is of a number of occurrences of variables, values, or variables and values. For a given variable or value in a given semantic system, the number of occurrences of other values and/or variable fields in the data set is determined. For example, a variable for Gender is selected. The number of CBC, breast cancer tests, aspirin prescriptions, colonoscopy, x-ray scans, and other variables associated with the occurrence of the Gender field for patients is counted. Similarly, the counts are made for variables—the number of other fields including gender occurring when a patient record has the aspirin prescription field. The counts for a variable may include in one distribution or provide separate distributions counts for values associated with the same variable and/or other variables. Similarly, distributions are calculated for values represented in the transaction data.

FIG. 2 shows three example distributions D1-3. Each of distributions D1 and D2 are from transaction data of a same semantic system, but are for different base variable or value. The distribution D3 is from transaction data of a different semantic system. Tens or hundreds of distributions may be calculated. Additionally or alternatively, other information than distribution may be used to derive statistics about the transaction data.

In act 50, the calculated distributions are compared. Any comparison may be used. For example, a statistical similarity is calculated. A difference in means, difference in standard deviations, chi-square, Kullback-Leiber (KL) divergence, correlation, and/or other measure of similarity may be used. The distribution for a given variable or value in one semantic set is compared to all or some of the distributions in the other semantic set. The distribution or distributions with the greatest similarity (i.e., least distance) are more likely associated with the same meaning (e.g., same variable or value). For example and referring to FIG. 2, D2 is more similar to D3 than D1 is to D3. Thus, the field or value for which D3 was calculated is more likely to mean or be the same as the field for which D2 was calculated, providing a hypothesis for a semantic link.

By repeating the comparisons for different variables and/or values, a set of links are created to represent the map. If any links have sufficient confidence, the corresponding distributions may be removed as options for linking with other variables or values. Alternatively, possibilities are not removed until all possible links have been tested. An iterative process may be used to select the most strongly linked (e.g., greatest similarity) and then subsequently select from remaining options. Other approaches may be used for linking, including using logic-based inclusion and exclusion of possible links or hypotheses.

The statistics of occurrence may be used alone to create the map. In other embodiments, other information in addition to the statistics is used. In act 48, other information is calculated. The map is created as a function of the statistical information from the service codes, patient data associated with the service codes, population statistics, and/or institution (e.g., system, department, or healthcare entity) information. A data mining solution is data driven and statistical in nature. The mappings are learned from transaction data from disparate sources. Transaction level, patient level, population level, system level and institution level information are used to form hypotheses. For example, amongst millions of laboratory transactions, 90% of the laboratory transactions refer to the same common tests. For example during a physical exam, one of the most common lab orders is a blood test for a lipid panel. Matching these distributions from various systems provides insights about which codes could be referring to the same tests in the disparate systems. In fact, it has been established that almost 90% of lab test transactions capture only 400 (out of the few thousand) LOINC codes, as the rest of the lab tests are rare in general patient populations. The most common or most rare lab tests may be identified and used for determining what information is used to create the map. In other embodiments, this statistical information is used as transaction data or in a same way as transaction data for creating the map. The non-transaction data may be used in an offline process for map creation. The 90% probability may be used to weight greater similarity measures, strengthening the match.

As another example, in addition to the statistical information from the data, knowledge such as 'linguistic' information in the descriptors is used. For example, if a descriptor has information about blood test or Hb (short for Hemoglobin), this information can be used to augment the hypotheses, ruling out possible links. A thesaurus may be used to logically rule in or out links or to weight links (more or less likely) based on descriptors with words that are synonyms or not. Similarly, units of measure may be used to rule out links.

The number of associated characteristics may be used. For example, variables have a number of possible values (e.g., 2 or 3 for gender). If the numbers are not within a threshold amount of each other, then the link is ruled out or reduced in weight (or vise versa). A variable with 25 possible values is not likely to have the same meaning as a variable with only 2 or 3 possible values. The number of patients for which a variable occurs may be used. If the relative frequencies are similar, the variables are more likely linked. Other number of associated characteristics may be used as additional statistics or information in addition to statistics.

The characteristics of the data field or value may be used. Descriptors, location of the field within the file structure, type of label (e.g., numerical, text, or numerical and text), field or value limitations (e.g., length of field—10 verses 100 characters), or other information is used to increase or decrease the likelihood of being linked.

The various input features from acts 46 and 48 are compared in act 50. Other information may be calculated from the input features to derive additional or alternative inputs, such as calculating characteristics of the distributions. As another example, the measures of similarities resulting from comparison are used as input features for further comparison. A cascade or hierarchal approach may be used.

To create the map with one or more links, the comparison of act 50 is implemented by a programmed processor. Any programming may be used, such as a sequence of rules or logic. Fuzzy logic techniques may be used. Unsupervised or semi-supervised machine learning is used. Where prior examples or samples of the different semantic systems are available, supervised machine learning may be used.

In one embodiment, the unsupervised or semi-supervised machine learning receives the transaction data, information calculated from the transaction data (e.g., the distributions), and/or other information and learns the links between variables and/or values in the different semantic systems. The values and/or variables with the same meaning are linked. Alternatively or additionally, the values and/or variables more likely to have the same meaning are identified for manual linking in the semi-supervised approach.

For unsupervised learning, the semantic links are made using unlabeled data. Any unsupervised machine learning may be used, such as clustering or blind signal separation with feature extraction for dimensionality reduction. For example, principle component analysis, independent component analysis, non-negative matrix factorization, or singular value decomposition are used. Combinations of techniques may be used. Neural network models, such as self-organizing maps or adaptive resonance theory may be used. The vigilance parameter may be pre-determined or provided during or as part of creating the map.

The statistical information (e.g., distributions, statistics derived from the distributions, measures of similarity, and/or other statistics related to the transaction data) is an input feature for the unsupervised learning. By performing the machine learning, the similarity or links forming the map are learned by the processor.

Either within the kernel for the machine learning or as part of use of an output of the machine learning, further limitations, constraints, logic, or other information may be used. The machine learning indicates a strength, such as a probability, similarity, or distance, of a link. The links above a threshold strength are possible links or hypotheses. Any threshold level may be used, such as a pre-determined probability or a number of highest hypotheses for any given variable or value. Possible links with strengths above the threshold are output, and possible links with strengths below the threshold are not output as hypotheses. An iterative fitting of hypotheses or user input may resolve conflicts where multiple possible links may occur for one or more variables or values.

The strengths may be altered prior to thresholding. For example, linguistics information is used in the machine learning kernel or on the outputs from the machine learning to rule out possible links. The descriptions may not include any synonyms, so the strength is reduced. As another example, a rule (e.g., pregnancy test only for female) or population statistics relating characteristics of the variables or values may rule out particular combinations or deal with common errors in statistics based linking. The rule or population information is included in the kernel for the machine learning or is applied to the output. Rather than absolute alteration (removing the hypothesis), the weight of the strength may be altered. For example, linguistic, text matching (billy direct~billy rubin direct), relationship in an ontology or medical thesaurus, or other information may be used to show that the strength (e.g., probability of proper linking or same meaning) should be increased or decreased. The amount of increase or decrease may be based on statistics, pre-determined, or otherwise set.

The creation of the map is performed once. The map may be then be used. Alternatively, the creation may be on-going or occur in real time. Calculating the distributions and comparing is performed for additional transactions for the healthcare entity received after previously comparing. An initial map is updated as more and more transactions are received. By repeatedly observing transactions as added during the course of the healthcare business, the hypotheses used for creating the map are proven or disproven. The newly created transaction data is added to the previous transaction data and the creation is performed independently of any existing map. Alternatively, the newly created transaction data is tested against the statistics and/or existing map to confirm or not proper semantic linking. This approach may also be used to correct any existing mappings that have been created manually. The transaction data is used to learn a map, and this learned map is compared to the manually created map. Any differences are highlighted for user decision.

In act 52, the created map is output. The map is a function of the comparison of distributions. Using the comparison of statistics from different sets of data, the map is created and output.

The map includes links between variables and/or values in one semantic system to variables and/or values in another semantic system. For example, Gender in one data set is linked to Sex in another data set. All or less than all of the variables and/or values of one data set may be linked to corresponding all or less than all of the variables and/or values of the other data set. The map may not be complete, but instead be a starting point for further manual mapping.

As more transactions are received, the links for mapping for variables and/or values not previously linked may be formed. The confidence in the linking may be sufficiently increased due to receiving additional transactions. Low confidence links transition to higher or sufficient confidence links. Coverage of the mapping gradually increases. Alternatively, the map is complete as initially formed.

In one embodiment, the output solicits user selection of possible links. Options based on the comparison calculations are provided. In some cases, given the paucity of data, more than one hypothesis may be plausible. Using thresholding, more than one possible link may result. Any number of possible links or hypotheses for a given variable or value may be output, such as two to five. For example, one link has a 45% probability and another link has a 55% probability where the threshold to establish a link is 90%. Human intervention is used to manually create the link. Both possible links, as well as descriptor or other extracts from the transaction data (e.g., sample messages), are output to the user. Using check boxes, graphic programming, or other user interface, the user is solicited to select one of the links and not another. Even with this manual involvement, the creation of the map is still considerably more efficient than manually creating the entire map as a human has to simply verify amongst a limited set. The manual intervention in the machine learning in the form of selection may be used to guide future learning. The selection itself may be used as an input in further learning so that the same information is more likely automatically linked in other map creations or in updates.

Sometimes, the hypotheses are strong as evidenced by the data, and there is only one final option for a particular field-field or value-value mapping. Human intervention is not used. The user merely selects files or data sets, activates the creation, and monitors output. The user does not select the link. The comparison and output for the link occur without user selection of the link.

After selection by the processor and/or the user, a final map includes one-to-one semantic linking of all values and/or variables of a given set. Less than all possible values or variables may be linked, such as where the map creation is configured to link only a predetermined sub-set of values and/or variables. Alternatively, the predetermined set of links is all of the values and variables. One data set may include one or more values or variables that do not exist in the other data set. Similarly, the number of occurrences may be sufficiently small, that statistical linking is non-determinative. The map may be created without linking such values or variables. Manual linking may be used for non-determinative values or variables.

Over time, profiles of these distributions and their corresponding maps are created. For some situations, typical types of profiles are created that may be applied in other situations. For example, at any given time, a new medical facility or entity is to be added to an existing system. The transactional data from the new medical entity is used to create a distribution. By comparing the new distributions to existing distributions from other medical entities, a hypothesis mapping is provided for any matches or sufficiently close matches.

In act 54, the created map is used. Information from one data set may be mapped to information from another data set. Since the semantic relationship is known, data may be aggregated from both semantic systems. Data federation, knowledge discovery (e.g., learning statistical relationships for diagnosis or treatment), inferencing, or other operation using a larger data set is performed. Mapping may be used to allow communication or interoperability between different systems. The map is used to translate.

Creating the map automatically using, at least in part, statistics from the data, may be used to reduce implementation time for healthcare information systems, such as hospital, physician, or lab systems. Disparate systems may communicate with each other in a seamless manner using the created map. The map is applied as part of hospital information exchange (HIE). The map may be created for commissioning a new computer network infrastructure or for adding a disparate system to an existing computer network infrastructure, such as when a healthcare entity decides to add a primary care practice within a physician network or decides to use a new lab provider.

FIG. 3 shows one embodiment of a system for automatic mapping of service codes in healthcare. The map between data sets with different semantics is created. The system implements the method of FIG. 1 or other methods.

The system includes one or more databases 12, 14, a processor 16, a memory 18, and a display 20. In one embodiment, the system is a server or computer. The processor 16, memory 18, and display 20 may be a standalone device or connected to a wired or wireless computer network. Additional, different, or fewer components may be provided. For example, additional databases 12, 14 are provided. As another example, the databases 12, 14 are not provided and the transaction data is stored in the memory 18.

Each database 12, 14 is a memory, buffer, or other structure for storing data. The databases 12, 14 store transaction data for different healthcare entities. Each healthcare entity is a hospital, institution, research facility, office, medical learning hospital, university, department, computer system, device, or other entity involved in communicating or storing transaction data. The healthcare entity may be involved in the treatment and/or diagnosis of patients. Routine data gathered for one or more patients is stored at each healthcare entity. The storage may be off-site, but is "at" the healthcare entity by being available for access at the healthcare entity.

The different healthcare entities have patient data for different sets of patients. The different healthcare entities may have the same or different standards of care, processes, treatments, patient approaches, devices, information technology infrastructures, management, or other care related approaches. Similarly, the types of patients (e.g., socio-economic, racial, or other differences) most common for the different healthcare entities may be similar or different. In one embodiment, the different healthcare entities are associated with treatment of patients in different counties, states, and/or countries. Due to any of these differences or for other reasons, one or more variables and/or one or more values may be labeled differently between the healthcare entities. Some variables and/or values may have the same semantic meaning and be labeled the same. The databases 12, 14 store transaction data using different semantic systems. The medical data is stored in different representations of the same thing (e.g., Gender vs. Sex or 1 verses Female).

The processor 16 accesses the transaction data from the databases 12, 14 as needed or to aggregate for creating the map translating across the different semantic systems. The processor 16 is configured by hardware and/or software to link values and/or variables of the medical data from the database 12 with values and/or variables of the medical data from the database 14. Alternatively, the processor 16 links from each database 12, 14 to a standard semantic system (i.e., a third semantic system). The links indicate corresponding semantic meaning in the representations.

The processor 16 creates the links using similarity of distribution of the values and/or variables in the sets of medical data. Any statistical analysis of the medical data and comparison between sets may be used. In one embodiment, the processor 16 applies unsupervised machine learning. The map of links between fields or values of the different sets of medical data is output from or using the machine learning.

The processor 16 is or is not affiliated or part of any of the healthcare entities and corresponding databases 12, 14. In one embodiment, the processor 16 is managed by a different entity than the healthcare entities and is a service provider of semantic maps. The processor 16 is located in a different building, campus, region, or geographic location than any of the healthcare entities. In other embodiments, one or more of the healthcare entities host and manage the processor 16. The processor 16 may or may not share a campus, building, or facility with one of the healthcare entities.

The processor 16 is a hardware device with processing implemented in various forms of hardware, software, firmware, special purpose processors, or a combination thereof. Some embodiments are implemented in software as a program tangibly embodied on a program storage device (e.g., the memory 18). The processor 16 may be a computer, personal computer, server, PACs workstation, imaging system, medical system, network processor, network, or other now know or later developed processing system. The processor 16 may be operatively coupled to other components, such as the memory 18 and the display 20. The processor 16 is implemented on a computer platform having hardware components. The other components include the memory 18, a network interface, an external storage, an input/output interface, the display 20, and/or a user input. Additional, different, or fewer components may be provided. The computer platform may also include an operating system and microinstruction code. The various processes, methods, acts, and functions described herein may be part of the microinstruction code or part of a program (or combination thereof) which is executed via the operating system.

A user interface is provided for creating the map. The user interface is at the processors 16. The user interface may be limited to arranging for learning of the map. In this configuration, the user may select an input features, statistics, data sets, variables and/or values to link, or other set-up options by selection, input, or from a menu. For creating the map from this arrangement information, further user input is not provided. Alternatively, the user guides a semi-supervised process, such as for selecting from a limited (e.g., 2-5) number of hypotheses for a link.

The user input may be a mouse, keyboard, track ball, touch screen, joystick, touch pad, buttons, knobs, sliders, combinations thereof, or other now known or later developed input device. The user input operates as part of a user interface. For example, one or more buttons are displayed on the display. The user input is used to control a pointer for selection and activation of the functions associated with the buttons. Alternatively, hard coded or fixed buttons may be used.

The user interface may include the display 20. The display 20 is a CRT, LCD, plasma, projector, monitor, printer, or other output device for showing data.

The processor 16 operates pursuant to instructions. The instructions and/or transaction data for creating the map are stored in a non-transitory computer readable memory such as an external storage, ROM, and/or RAM. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The same or different computer readable media may be used for the instructions, the transaction data, and the map. The transaction data are stored in an external storage (databases 12, 14), but may be in other memories. The external storage may be implemented using a database management system (DBMS) managed by a processor and residing on a memory, such as a hard disk, RAM, or removable media. Alternatively, the storage is internal to the processor 16 (e.g. cache). The external storage may be implemented on one or more additional computer systems. For example, the external storage may include a data warehouse system residing on a separate computer system, a PACS system, or any other now known or later developed hospital, medical institution, medical office, testing facility, pharmacy, lab, or other medical patient record storage system. The external storage, an internal storage, other computer readable media, or combinations thereof store data for at least one patient record for a patient. The patient record data may be distributed among multiple storage devices.

The processor 16 has any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor. The processor implements the program alone or includes multiple processors in a network or system for parallel or sequential processing.

In the arrangement of FIG. 3, the processor 16 and the databases 12, 14 communicate through one or more networks. Wired and/or wireless communications are used. The networks may be local area, wide area, public, private, enterprise, or other networks. Any communication format may be used, such as e-mail, text, or TCP/IP. Direct or indirection communication is provided. The communications may or may not be secured, such as using a public key infrastructure. Alternatively, the communication is by manual data transfer, such as using a memory stick.

It is to be understood that the present embodiments may be implemented in various forms of hardware, software, firmware, special purpose processors, or a combination thereof. Preferably, the present embodiments are implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps are preferably implemented in software, the actual connections between the system components (or the process steps) may differ depending upon the manner in which the present invention is programmed.

While this invention has been described in conjunction with the specific embodiments outlined above, it is evident that many alternatives, modifications, and variations will be apparent o those skilled in the art. Accordingly, the preferred embodiments of the invention as set forth above are intended to be illustrative, not limiting. A variety of modifications to the embodiments described will be apparent to those skilled in the art from the disclosure provided herein. Thus, the present invention may be embodied in other specific forms without departing from the spirit or essential attributes thereof.

We claim:

1. A method for automatic mapping of semantics in healthcare, the method comprising:

accessing first transaction data of a first healthcare entity in a first database, the first transaction data having a first set of values for a plurality of fields corresponding to a first semantic system;

calculating, by a processor, a first distribution of the first set of values in the first transaction data, wherein the first distribution corresponds to the first semantic system;

accessing second transaction data of a second healthcare entity in a second database, the second transaction data having a second set of values for a plurality of fields corresponding to a second semantic system that is different than the first semantic system;

calculating, by the processor, a second distribution of the second set of values in the second transaction data, wherein the second distribution corresponds to the second semantic system;

comparing, by the processor, the statistical similarity of the first distribution corresponding to the first semantic system and the second distribution corresponding to the second semantic system that is different than the first semantic system with machine learning, wherein comparing includes:

determining a probability that a first field in the plurality of fields corresponding to the first semantic system is a particular field type based on a number of distinct values for the first field, determining a probability that a second field in the plurality of fields corresponding to the second semantic system is the particular field type based on a number of distinct values for the second field, and when it is determined that the number of distinct values of the first field of the first semantic system and the number of distinct values of the second field of the second semantic system are not within a predetermined threshold of one another, determining the first field and the second field are not the same particular field type;

automatically outputting, from the machine learning, a map relating syntax of the first transaction data of the first semantic system to syntax of the second transaction data of the second semantic system, the map being a function of the comparing the statistical similarity of the first distribution corresponding to the first semantic system and the second distribution corresponding to the second semantic system;

using the map for semantic interoperability between the first and second semantic systems, communicating information between the first and second healthcare entities; and updating the map each time new transaction data of the first healthcare entity is accessed, wherein updating the map includes:
re-calculating the first distribution using the new transaction data; and
comparing the statistical similarity of the first distribution, as updated, to the second distribution.

2. The method of claim 1 wherein accessing the first transaction data of the first healthcare entity in the first database comprises accessing one or more computerized orders, results, or services of the first healthcare entity.

3. The method of claim 1 wherein the first transaction data represents one or more variables and values for the variables, wherein the one or more variables and values are labeled differently in the first semantic system than in the second semantic system.

4. The method of claim 1 wherein calculating the first distribution comprises counting occurrences for one or more of: a plurality of variables of the first transaction data and values of the first transaction data, a selected variable for the first transaction data, and a selected value of the first transaction data.

5. The method of claim 1 wherein comparing, by the processor, the statistical similarity of the first distribution and the second distribution with machine learning comprises determining the statistical similarity of the first distribution and the second distribution, wherein distributions with a greater similarity are likely associated with the same meaning.

6. The method of claim 1 wherein comparing, by the processor, the statistical similarity of the first distribution and the second distribution with machine learning comprises performing unsupervised machine learning.

7. The method of claim 1 wherein comparing, by the processor, the statistical similarity of the first distribution and the second distribution with machine learning comprises comparing, for the first and second distributions, one or more of linguistic information, number of associated characteristics, and data field characteristics as input features for the machine learning.

8. The method of claim 1 further comprising upon receiving additional transactions for the first healthcare entity, calculating a subsequent first distribution for comparison to the second distribution.

9. The method of claim 1 wherein automatically outputting, from the machine learning, the map relating the first semantic system to the second semantic system further comprises outputting semantic links between variables, values, or variables and values for the first dataset with variables, values, or variables and values for the second dataset.

10. The method of claim 1 wherein automatically outputting, from the machine learning, the map relating the first semantic system to the second semantic system comprises:
outputting two to five possible semantic links; and
soliciting user selection of at least one of the two to five possible links.

11. The method of claim 1 wherein automatically outputting, from the machine learning, the map relating the first semantic system to the second semantic system further comprises outputting, without user selection, one-to-one semantic linking of all values, variables, or values and variables of a predetermined set.

12. The method of claim 1 further comprising mapping the first set of values for the plurality of fields corresponding to the first semantic system to the second set of values for the plurality of fields corresponding to the second semantic system.

13. In a non-transitory computer readable storage medium having stored therein data representing instructions executable by a programmed processor for automatic mapping of service codes in healthcare, the storage medium comprising instructions for:
obtaining service codes from transaction data of disparate healthcare entities, each of the disparate healthcare entities utilizing different sematic systems, wherein the service codes are associated with a different semantic system for each of the disparate healthcare entities;
calculating one or more distributions for the service codes of each of the different semantic systems, wherein a first plurality of values that correspond to services codes in a first semantic system are used to calculate distributions specific to a first semantic system, and wherein a second plurality of values that correspond to services codes in a second semantic system are used to calculate distributions specific to the second semantic system;
determining, for each of the services codes in each of the different semantic systems:
a probability that a first service code is a particular type based on a count of distinct values present in the first plurality of values of the first semantic system that are used for the first service code in the transaction data,
a probability that a second service code is a particular type based on a count of distinct values present in the second plurality of values of the second semantic system that are used for the second service code in the transaction data, and
when it is determined that the count of distinct values of the first service code of the first semantic system and the count of distinct values of the second service code of the second semantic system are not within a predetermined threshold of one another, determining the first service code and the second service code are not the same particular type;
creating, by the programmed processor using the one or more semantic-system-specific distributions calculated for the service codes of each of the different semantic systems and the determinations for each of the services codes in each of the different semantic systems, a map relating the plurality of service codes across the different semantic systems, the map created as a function of statistical information that indicates a level of similarity between at least two of the plurality of service codes across the different semantic systems, wherein the map further relates syntax of the first plurality of values that correspond to services codes in the first semantic system to the syntax of the second plurality of values that correspond to service codes in the second semantic system;

using the map for semantic interoperability between the different semantic systems, communicating information between the disparate healthcare entities using the map for direct semantic interoperability; and updating the map when new transaction data of the disparate healthcare entities is accessed, wherein updating the map includes:

re-calculating the one or more distributions for the service codes, and updating the determinations for each of the services codes in each of the different semantic systems.

14. The non-transitory computer readable storage medium of claim 13 wherein obtaining the service codes from disparate healthcare entities comprises obtaining the service codes as variables of medical data.

15. The non-transitory computer readable storage medium of claim 13 wherein creating the map relating the plurality of service codes having different semantics is performed with unsupervised machine learning and the statistical information is an input feature that includes at least one characteristic of a distribution of values, variables, or values and variables of the service codes relative to each other.

16. The non-transitory computer readable storage medium of claim 13 wherein the map relating the plurality of service codes having different semantics is a function of the statistical information from one or more of the service codes, patient data associated with the service codes, population statistics, and institution information.

17. The non-transitory computer readable storage medium of claim 13 wherein creating the map relating the plurality of service codes having different semantics is performed comprises:

calculating strengths of possible semantic links;
applying the strengths to a threshold; and
outputting the possible semantic links having strengths at or above the threshold.

18. A system for automatic mapping of service codes in healthcare, the system comprising:

a memory configured to store first medical data in a first representation and store second medical data in a separate second representation, wherein the first medical data corresponds to a first semantic system and the second medical data corresponds to a second semantic system different than the first semantic system; and a processor configured to:

determine a level of similarity between values, variables, and values and variables, for each variable in the first medical data and each variable in the second medical data:

(1) determine a probability that a first variable of the first medical data corresponding to the first semantic system is a particular field type based on a count of distinct values used for the first variable in the first medical data;

(2) determine a probability that a second variable of the second medical data corresponding to the second semantic system is the particular type based on a count of distinct values used for the second variable in the second medical data;

(3) determine whether the count of distinct values used for the first variable in the first medical data is within a predetermined threshold of the count of distinct values used for the second variable in the second medical data;

(4) when the counts are within the predetermined threshold, increase a probability that the first variable and the second variable are the same particular type; and (5) when the counts are not within the predetermined threshold, increase a probability that the first variable and the second variable are not the same particular type;

determine, using the level of similarity between the values, variables, or values and variables, corresponding semantic meanings between the first representation of the first medical data of the first semantic system and second representation of the second medical data of the second semantic system;

based on the level of similarity determined and the semantic meanings determined, building a map that relates syntax of the first medical data of the first semantic system to syntax of the second medical data of the second semantic system, the map comprising semantic links between values, variables, or values and variables of the first medical data that corresponds to the first semantic system with values, variables, or values and variables of the second medical data that corresponds to the second semantic system;

communicate information between the first and second semantic systems for direct semantic interoperability; and when one or more of the first or second medical data are updated, re-determine the level of similarity between linked values, linked variables, and linked values and variables in view of the one or more of the first or second medical data as updated.

19. The system of claim 18 wherein the processor is further configured to apply unsupervised machine learning in building the map comprising links of the values, variables, or values and variables of the first and second medical data.

20. The system of claim 18 wherein the processor is further configured to link, as a function of similarity of distribution, the values, variables, or values and variables of the first and second medical data.

21. The system of claim 20 wherein the processor is further configured to:

compare a distribution of the first medical data to a distribution of the second medical data; and
generate a link as a function of the comparison.

22. The system of claim 20 wherein the processor links values, variables, or values and variables of the first medical data that corresponds to the first semantic system with values, variables, or values and variables of the second medical data that corresponds to the second semantic system as a function of a previous selection of possible links.

23. The system of claim 18 wherein the processor is further configured to update the links as additional medical data is received.

* * * * *

UNITED STATES PATENT AND TRADEMARK OFFICE
CERTIFICATE OF CORRECTION

| | |
|---|---|
| PATENT NO. | : 10,403,391 B2 |
| APPLICATION NO. | : 14/037548 |
| DATED | : September 3, 2019 |
| INVENTOR(S) | : Faisal Farooq et al. |

It is certified that error appears in the above-identified patent and that said Letters Patent is hereby corrected as shown below:

On the Title Page

Item (72) Inventors, Line 02: Please remove "Zionville" and replace with --Zionsville--.

Page 03, Column 01, Line 34: Please remove "oxymown" and replace with --oxymoron--.

Signed and Sealed this
Twenty-second Day of October, 2019

Andrei Iancu
*Director of the United States Patent and Trademark Office*